US00PP30147P2

(12) United States Plant Patent
Farrow

(10) Patent No.: US PP30,147 P2
(45) Date of Patent: Jan. 29, 2019

(54) ***ILEX* PLANT NAMED 'ILEXFARROWTRACEY'**

(50) Latin Name: *Ilex glabra*
Varietal Denomination: ILEXFARROW-TRACEY

(71) Applicant: Michael Wayne Farrow, Warwick, MD (US)

(72) Inventor: Michael Wayne Farrow, Warwick, MD (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,611

(22) Filed: Nov. 30, 2017

(51) Int. Cl.
*A01H 5/00* (2018.01)

(52) U.S. Cl.
USPC ..... Plt./247
CPC ..... *A01H 5/00* (2013.01)

(58) Field of Classification Search
USPC ..... Plt./247
CPC ..... A01H 5/00; A01H 5/12
See application file for complete search history.

*Primary Examiner* — Kent L Bell
(74) *Attorney, Agent, or Firm* — Cassandra Bright

(57) ABSTRACT

A new and distinct *Ilex glabra* cultivar named 'ILEXFARROWTRACEY' is disclosed, characterized by dark green foliage. Plants are dwarf and compact, forming dense mounds, with foliage growth to the ground. The new cultivar is an *Ilex glabra*, suitable for ornamental garden purposes.

2 Drawing Sheets

Latin name of the genus and species: *Ilex glabra*.
Variety denomination: 'ILEXFARROWTRACEY'.

BACKGROUND OF THE INVENTION

The new cultivar is a product of a planned breeding program by the inventor. The new variety, hereinafter referred to as 'ILEXFARROWTRACEY' was selected from an open-pollination breeding program conducted during 2007. The seed parent is *Ilex glabra* 'Shamrock', unpatented. The pollen parent is unidentified. The novel variety was discovered in a commercial nursery in Warwick, Md. during 2008.

After identifying the new variety as a potentially interesting selection, first asexual propagation of 'ILEXFARROWTRACEY' occurred by softwood cuttings at a commercial nursery in Warwick, Md. in June 2009. The inventor continued controlled testing and asexual propagation, assessing stability of the unique characteristics of this variety. Eight generations have been asexually reproduced and have shown that the unique features of this cultivar are stable and reproduced true to type.

SUMMARY OF THE INVENTION

The cultivar 'ILEXFARROWTRACEY' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ILEXFARROWTRACEY' These characteristics in combination distinguish 'ILEXFARROWTRACEY' as a new and distinct *Ilex glabra* cultivar:

1. Dwarf, compact plant habit.
2. Dark foliage.

3. No blight issues observed, plant may be resistant to Phytophthora ilicis and/or other foliar pathogens of *Ilex*.
4. Foliage covers the plant attractively all the way to the ground.

COMMERCIAL COMPARISON

'ILEXFARROWTRACEY' can be compared to the commercial variety *Ilex glabra* 'SMNIGAB17' U.S. Plant Pat. No. 27,554. The varieties are similar in most horticultural characteristics, however, plants of 'ILEXFARROWTRACEY' differ in the following ways:

1. New cultivar has larger leaves than this comparator.
2. New cultivar has dark green foliage; comparator has red tips during spring flush.

PARENTAL COMPARISON

'ILEXFARROWTRACEY' can be compared to the parent *Ilex glabra* 'Shamrock'. The varieties are similar in most horticultural characteristics, however, plants of 'ILEXFARROWTRACEY' differ in the following ways:

1. New cultivar is of smaller stature; parent is taller by about 3 feet.
2. The seed parent may lose foliage near the ground, which is not regenerated, leaving the base of the plant bare.
3. The new variety has a more mounding plant habit, the seed parent is more upright.

BRIEF DESCRIPTION OF THE PHOTOGRAPHS

Figure 1:
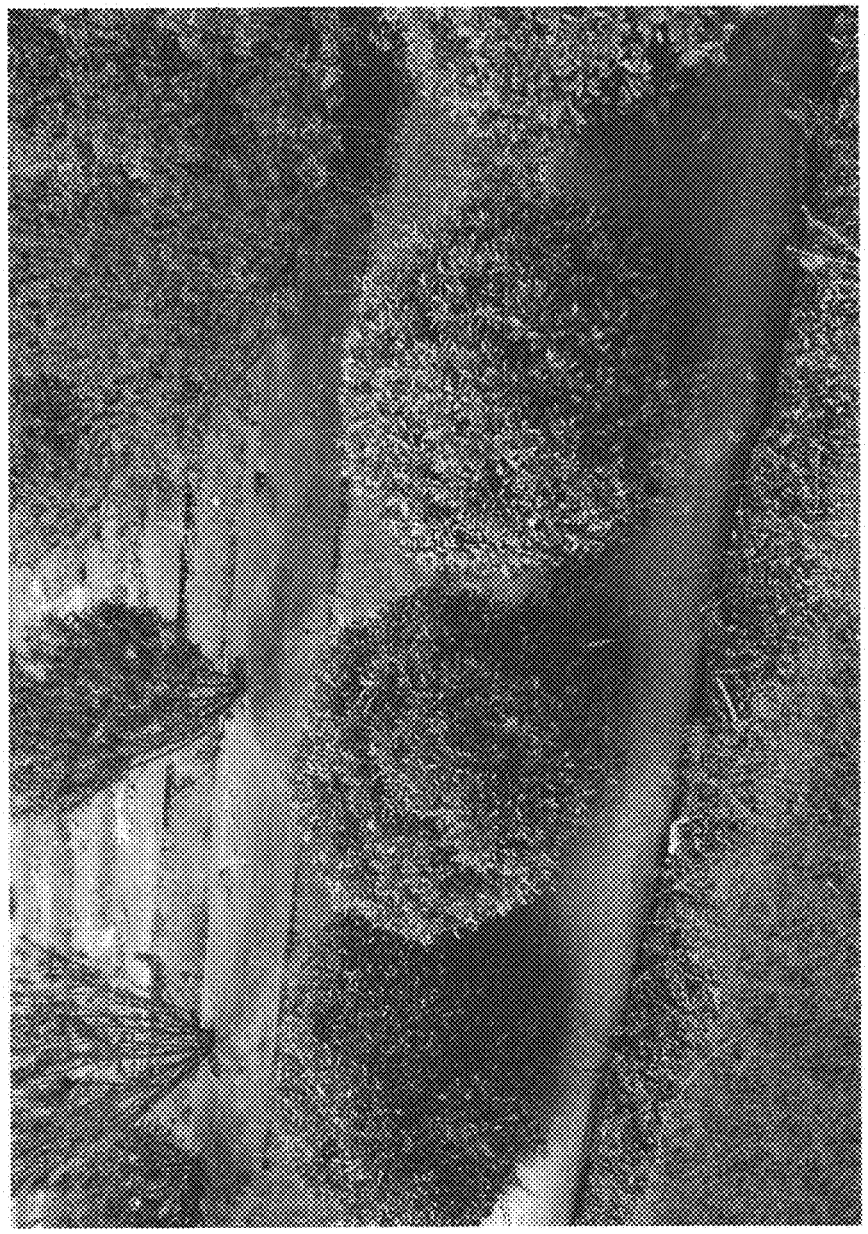

The accompanying photograph in FIG. 1 illustrates in full color a typical plant of 'ILEXFARROWTRACEY' grown outdoors in Grand Haven, Mich. Plants in FIG. 1 are approximately 3 years old, and exhibit the characteristic full, compact and mounded growth.

Figure 2:
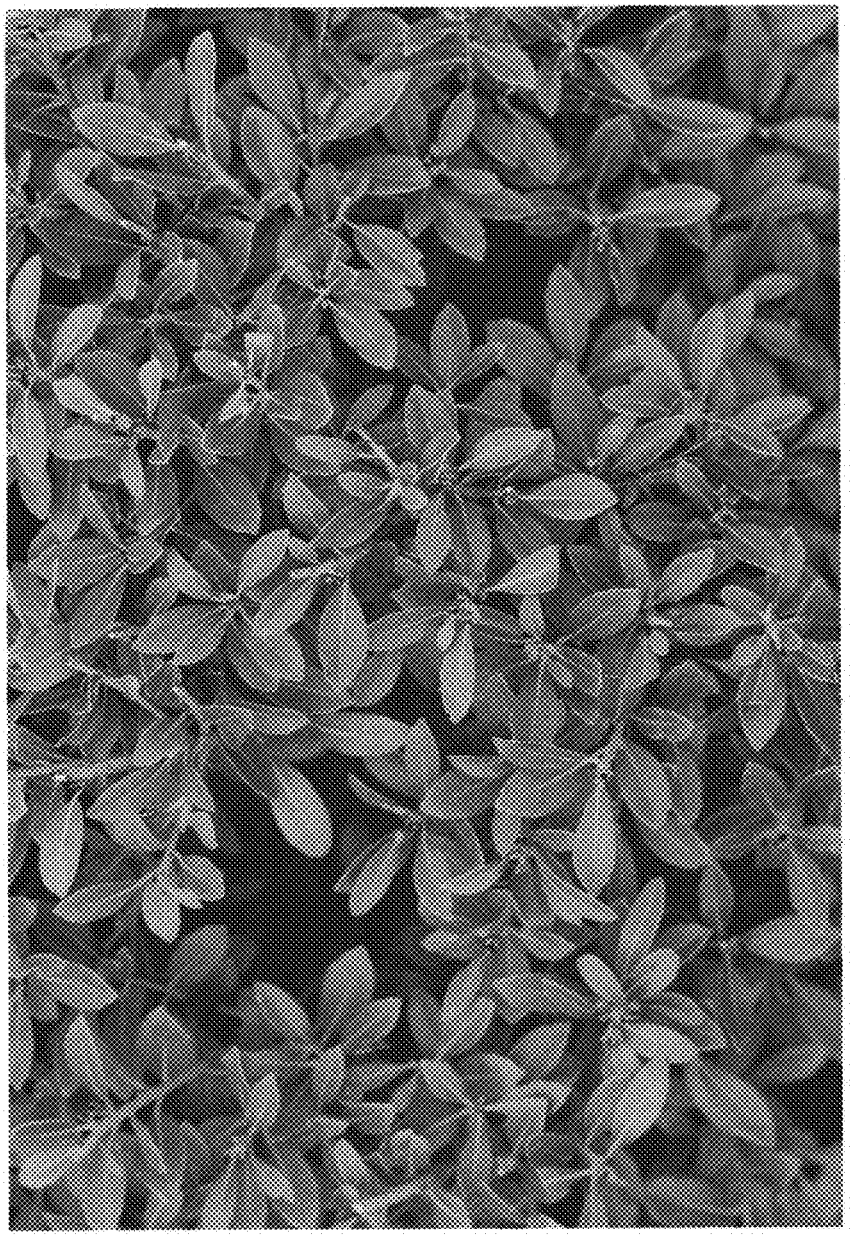

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'ILEXFARROWTRACEY' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Ilex glabra* 'ILEXFARROWTRACEY'.

PROPAGATION

Typical method: Softwood cuttings.

Time to initiate rooting: 30 days during summer; 45 days during winter.

Time to produce a rooted young plant: 150 days during summer; 5 months during winter.

Root description: Dense and fibrous roots present. Freely branching, medium thickness, dark colored.

PLANT

Age of plant described: 2 to 3 years.

Container size of plant described: 3 gallon.

Growth habit: Perennial shrub, compact and mounded.

Height: 19 cm.

Plant spread: 43 cm.

Typical growth rate: Good.

Branching characteristics: Many branches forming a dense, round plant.

Angle: About 45°, outward and upward.

Quantity of lateral branches: 10.

Length of lateral branches: 23 cm.

Diameter of lateral branches: 4 mm.

Lateral branch shape: Round.

Stem strength: Strong.

Stem color:

*New wood*.—Yellow green 144C.

*Old wood*.—Greyed-brown 199A.

Internode length: 12 mm.

FOLIAGE

Leaf:

*Arrangement*.—Alternate.

*Shape of blade*.—Elliptic.

*Apex*.—Acute.

*Base*.—Cuneate.

*Margin*.—Mostly entire, more sinuate near tip.

*Length*.—3.35 cm.

*Width*.—1.5 cm.

*Texture of top surface*.—Very smooth and soft.

*Texture of bottom surface*.—Smooth, kind of dry.

*Foliage color*.—Young leaves, upper side: Green 139A. Young leaves, under side: Green 138B. Mature leaves, upper side: Green 139A. Mature leaves, under side: Green 138B.

*Venation*.—Pinnate.

*Fragrance*.—Not observed.

*Petiole*.—Texture, upper side: Smooth, some pubescence. Texture, under side: Smooth, some pubescence. Color, upper side: Green 138D. Color, under side: Green 138D.

FLOWER

Flowering not observed.

OTHER CHARACTERISTICS

Disease and pest resistance: Neither resistance nor susceptibility observed.

Drought tolerance: No tolerance for drought.

Temperature tolerance: −32 to 36 C.

What is claimed is:

1. A new and distinct cultivar of *Ilex glabra* plant named 'ILEXFARROWTRACEY' as herein illustrated and described.

* * * * *